United States Patent [19]

Biertuempel et al.

[11] Patent Number: 6,060,621
[45] Date of Patent: May 9, 2000

[54] PROCESS FOR THE PREPARATION OF METHANESULFONIC ACID

[75] Inventors: Ingo Biertuempel, Dusseldorf; Klaus Driemel, Duisburg; Joachim Van De Flierdt; Dieter M.M. Rohe, both of Dinslaken, all of Germany

[73] Assignee: Grillo-Werke A.G., Duisburg, Germany

[21] Appl. No.: 09/163,909

[22] Filed: Oct. 1, 1998

[30] Foreign Application Priority Data

Oct. 4, 1997 [DE] Germany .......................... 197 43 901

[51] Int. Cl.$^7$ .................................................. C07C 303/02
[52] U.S. Cl. ............................ 562/115; 558/39; 562/30; 562/118; 562/120; 562/123
[58] Field of Search ................ 558/39; 562/30, 562/115, 118, 120, 123

[56] References Cited

FOREIGN PATENT DOCUMENTS

| 101 817 | 2/1923 | Germany . |
| 101 818 | 2/1923 | Germany . |
| 1313853 A1 | 10/1985 | U.S.S.R. . |
| 1313853 | 5/1987 | U.S.S.R. ................................ 562/118 |

OTHER PUBLICATIONS

Pantlischko et al., Monatshefte Für Chemie, zBd. 89, 1958, Seiten 285–287, XP002092953, Seite 287, Zeilen 1–3, 12–26.

P.K. Dutt, J. Chem. Soc., 125 1924, pp. 1463–1465, XP002092954.

Database Chemabs Chemical Abstracts Services, Columbus, Ohio, Accession No. 77:33931, SP002092955.

Katschurin, Erfindungsbeschreibung, 335240.

Lober et al., Sulfonsäuren, pp. 567–550.

Primary Examiner—Peter O'Sullivan
Attorney, Agent, or Firm—Jacobson, Price, Holman & Stern, PLLC

[57] ABSTRACT

The process for the preparation of methanesulfonic acid by reacting sulfite ions within an aqueous system with dimethyl sulfate at an elevated temperature and adding a strong acid subsequently, wherein the molar ratio of sulfite ions to dimethyl sulfate is 1.5 to 2.5:1, preferably 2:1, and the reaction charge is maintained at said elevated temperature for at least 2 h, preferably 4 h.

6 Claims, No Drawings

PROCESS FOR THE PREPARATION OF METHANESULFONIC ACID

The present invention pertains to a process for the preparation of methanesulfonic acid.

Methanesulfonic acid, which is a colorless substance having a melting point of 20° C., is a strong acid acting corroding but not oxidizing.

Methanesulfonic acid is used in the electroplating industry and for organic syntheses, in particular as a catalyst for alkylations, esterifications, and polymerizations. Beyond that, methanesulfonic acid is used as a starting material for the preparation of methanesulfonyl chloride.

Methanesulfonic acid is produced predominantly by oxidizing methylthiol or dimethyl disulfide using nitric acid, hydrogen peroxide, chlorine or by employing electrochemical processes.

Moreover, reacting sodium sulfite with dimethyl sulfate is known; cf. Ullmanns Encyklopädie der technischen Chemie, Vol. 16, 1965, pp. 576/550.

From the specification of the invention of the inventor's certificate of USSR 335240 published on May 25, 1972, there can be learned a process for obtaining methanesulfonic acid, wherein equimolar amounts of basic sulfites are reacted with dimethyl sulfate by adding dimethyl sulfate to a saturated solution of a basic sulfite during about 20 minutes while heating the reaction mass to 97–99° C., the obtained reaction mass is allowed to stand for a period not exceeding 35 minutes, subsequently treated with concentrated sulfuric acid and subjected to a vacuum distillation and the product is purified by procedures well-known in the art.

Here, the reaction of dimethyl sulfate with sodium sulfite is represented by the following reaction equation:

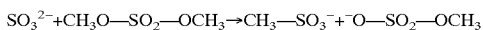

$$SO_3^{2-}+CH_3O-SO_2-OCH_3 \rightarrow CH_3-SO_3^- + {}^-O-SO_2-OCH_3$$

This process is detrimental in that only one methyl group of the dimethyl sulfate is used and the side product, methyl sulfate, forms free methylsulfuric acid at pH values below 7, said methylsulfuric acid being in equilibrium with sulfuric acid and the toxicologically questionable dimethyl sulfate.

Consequently, it is the object of the present invention to develop a process for the preparation of methanesulfonic acid starting from dimethyl sulfate and sodium sulfite which—based on dimethyl sulfate—produces higher yields without forming side products which may form dimethyl sulfate anew and uncontrolledly in the waste water later.

The object of the invention is solved by a process having the features of claim 1.

In the process of the invention sulfite ions and dimethyl sulfate are reacted within an aqueous system at elevated temperatures, the molar ratio of sulfite ions to dimethylsulfate being of from 1.5 to 2.5:1, preferably 2:1, and the reaction charge being kept at said elevated temperature for at least two hours, preferably four hours, and the methanesulfonic acid is liberated by a subsequent reaction with a strong acid.

The reaction equation of the process of the invention is:

$$2SO_3^{2-}+CH_3O-SO_2-OCH_3 \rightarrow 2CH_3-SO_3^- + SO_4^{2-}$$

The process of the invention achieves the transfer of both methyl groups from dimethyl sulfate to the sulfite ions by increasing the ratio of sulfite ions to dimethyl sulfate and increasing the reaction time distinctly.

In addition to the theoretical yield, based on dimethyl sulfate, being doubled in this manner there is formed free sulfate as a side product which, in the form of the salt thereof, e.g., sodium sulfate, is toxicologically safe.

Preferably, the pH value of the reaction charge is maintained in a range being greater of or equal to 6 and optionally adjusted to this range by adding a base such as NaOH.

In the process of the invention the sulfite ions can be provided in the form of a sulfite salt, e.g., sodium, potassium, or ammonium sulfite, or as substances forming sulfite ions within the reaction charge such as, e.g., sodium pyrosulfite ($Na_2S_2O_5$).

The preferred reaction temperature is above 60° C. and more preferred above 95° C., such that the reaction process may be effected particularly simple by refluxing. If desired, the reaction may be performed under increased pressure, e.g., 2 to 5 bar. Preferably, however, normal pressure or even a slightly reduced pressure will be employed for reasons of cost and safety.

Subsequently, the process of the invention is continued by reacting with a strong acid, e.g., sulfuric acid, and purifying the methanesulfonic acid, e.g., by distillation.

The following example shall illustrate the process of the invention.

A suspension of 300 g (2.38 mol) of sodium sulfite in 1.1 l water is heated to 95–100° C. in a 2 l three-necked flask equipped with a stirrer, an internal thermometer, a dropping funnel, and a reflux condenser. At this temperature there is a clear solution. Within 30 minutes 135 g (1.07 mol) of dimethyl sulfate are added dropwise. Subsequently the solution is stirred at 90–100° C. for 4 h. During this time the pH value of the solution is monitored. If the pH value decreases below 6.0, a 20% solution of sodium sulfite is added dropwise until the pH value exceeds a value of 7.0. Thereafter, 450 g of concentrated $H_2SO_4$ are added to the reaction charge, which is then distilled carefully at a pressure below 3 kPa.

Repeating the reaction at pressures up to 5 bar likewise results in good and high yields, based on the used dimethyl sulfate, that is, 75 to 85%.

What is claimed is:

1. A process for the preparation of methanesulfonic acid comprising reacting sulfite ions within an aqueous system with dimethyl sulfate at an elevated temperature and, subsequently, adding a strong acid, wherein the molar ratio of sulfite ions to dimethyl sulfate is 1.5 to 2.5:1, and the reaction is maintained at said elevated temperature for at least 2 h.

2. The process according to claim 1, wherein the reaction is maintained in a pH range greater than or equal to 6 by adding a base.

3. The process according to claim 1, wherein the sulfite ions are provided in the form of sodium pyrosulfite.

4. The process according to claim 1, wherein the reaction is performed at a temperature greater than or equal to 95° C.

5. The process according to claim 1, wherein the molar ratio of sulfite ions to dimethyl sulfate is 2:1.

6. The process according to claim 1, wherein the reaction is maintained at said elevated temperature for 4 hours.

* * * * *